United States Patent [19]

Hunt

[11] Patent Number: 4,717,414

[45] Date of Patent: Jan. 5, 1988

[54] HERBICIDALLY ACTIVE IMIDAZOPYRROLO-PYRIDINE (OR BENZENE) DERIVATIVES

[75] Inventor: David A. Hunt, Copley, Ohio

[73] Assignee: PPG Industries, Inc., Pittsburgh, Pa.

[21] Appl. No.: 894,590

[22] Filed: Aug. 8, 1986

[51] Int. Cl.$^4$ .................. A01N 43/48; C07D 471/00; C07D 491/00; C07D 235/00

[52] U.S. Cl. .......................................... 71/92; 546/82; 548/302

[58] Field of Search ................... 546/82, 64; 548/302; 71/92

[56] References Cited

U.S. PATENT DOCUMENTS 3,917,599 11/1975 Saxena et al. .................. 546/64

Primary Examiner—Henry R. Jiles
Assistant Examiner—Robert C. Whittenbaugh
Attorney, Agent, or Firm—Edward J. Whitfield

[57] ABSTRACT

The invention relates to imidazopyrrolo-pyridine (or benzene) derivatives having herbicidal activity, herbicidal compositions thereof and the use thereof to control plant growth.

4 Claims, 4 Drawing Figures

FIGURE I:
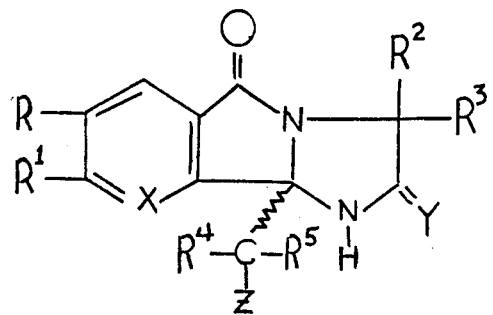
FIGURE II:
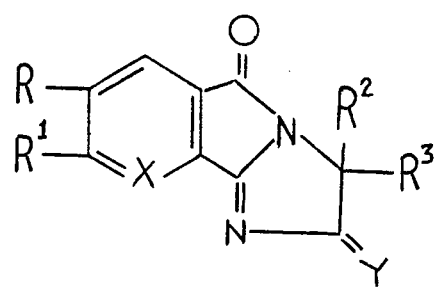
FIGURE III:
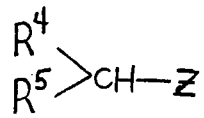
FIGURE IV:
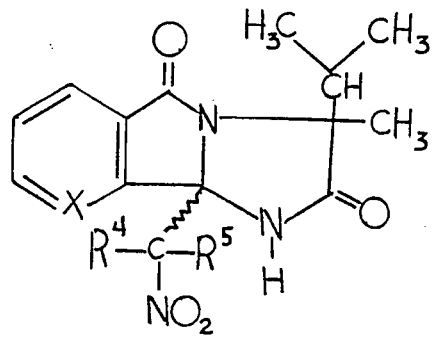

HERBICIDALLY ACTIVE IMIDAZOPYRROLO-PYRIDINE (OR BENZENE) DERIVATIVES

FIELD OF THE INVENTION

This invention relates to imidazopyrrolo-pyridine (or benzene) derivatives having herbicidal activity, herbicidal compositions thereof and the use thereof to control plant growth.

THE DRAWINGS

FIG. I depicts, by structural formula, the compounds of this invention.

FIG. II depicts, by structural formula, a starting material used to prepare the compounds of this invention.

FIG. III depicts, by structural formula, a starting material used to prepare the compounds of this invention.

FIG. IV depicts, by structural formula, the compounds of this invention prepared as described in the working Examples.

THE INVENTION

This invention provides imidazopyrrolo-pyridine (or benzene) compounds having the structural formula depicted in FIG. I wherein:

R and $R^1$ are the same or different and represent hydrogen, alkenyl; halogen, $C_1$ to $C_4$ alkyl, alkoxy, alkylthio or haloalkyl; up to $C_6$ alkenyl or alkynyl; phenyl, substituted phenyl or substituted phenyl alkyl; or R and $R^1$ together may form a saturated or unsaturated ring containing up to 4 carbon atoms which may be optionally substituted or interrupted by up to 3 hetero atoms;

$R^2$ and $R^3$ are the same or different and represent $C_1$ to $C_4$ alkyl, haloalkyl or alkoxy;

X is CH or nitrogen;

Y is oxygen or sulfur;

Z is nitro, amino, cyano or —$COOR^6$ wherein $R^6$ is hydrogen, alkali metal or $C_1$ to $C_4$ alkyl;

$R^4$ is hydrogen, $C_1$ to $C_4$ alkyl, haloalkyl, alkoxy or alkylthio; or up to $C_6$ alkenyl or alkynyl; and $R^5$ is Z or $R^4$.

Preferred Formula I compounds are those wherein R and $R^1$, are hydrogen; $R^2$ and $R^3$ are alkyl; X is nitrogen; Y is oxygen; Z is nitro; and $R^4$ and $R^5$ are independently hydrogen or alkyl.

The Formula I compounds may be prepared by reacting a compound having the structural formula depicted in FIG. II wherein: R, $R^1$, $R^2$, $R^3$, X and Y are previously defined with a the alkali metal salt of compound having the structural formula depicted in FIG. III wherein: $R^4$, $R^5$ and Z are as previously defined. The reaction is typically conducted in the presence of a polar solvent such as tetrahydrofuran or dimethylsulfoxide at temperatures ranging from ambient to reflux.

The invention is illustrated, but is not intended to be limited, by the following Examples which describe preparation of certain of the Formula I compounds.

EXAMPLE I

Preparation of:
3-Isopropyl-3-Methyl-9-Nitromethyl-5H-Imidazo-[1',2':1,2]-Pyrrolo-[3,4b]-Pyridine-2-(3H, 9H)-5-Dione A mixture of 5.0 grams (20.5 mmoles) of 3-isopropyl-3-methyl-5H-imidazo-[1'2':1,2]-pyrrolo-[3,4b]-pyridine-2-(3H,9H)-5-dione, 3.39 grams (55.55 mmoles) of nitromethane, 9.20 grams (66.66 mmoles) of potassium carbonate and 100 milliliters of dry dimethyl sulfoxide was stirred at room temperature, under a nitrogen atmosphere for about 4 hours. The mixture was then poured into 200 milliliters of water and the pH was adjusted to 4–5 with concentrated hydrochloric acid. The mixture was then extracted with 2×150 milliliter portions of methylene chloride and the organic extracts were washed with 2×300 milliliter portions of water, then dried over anhydrous magnesium sulfate and filtered. The filtrate was concentrated in vacuo affording 5.02 grams of a pale yellow foam confirmed by NMR and MS as the desired product.

EXAMPLE II

Preparation of:
3-Isopropyl-3-Methyl-9-(1-Nitro-1-Ethylmethyl)-5H-Imidazo-[1'2':1,2]-Pyrrolo-[3,4b]-Pyridine-2-(3H)-5-Dione A mixture of 11.0 grams (4.12 mmoles) of 3-isopropyl-3-methyl-5H-imidazo-[1'2':1,2]-pyrrolo-[3,4b]-pyridine-2-(3H, 9H)-5-dione, 1.72 grams (19.3 mmoles) of 1-nitropropane, 0.102 gram (4.25 mmoles) of sodium hydride and 60 milliliters of tetrahydrofuran was heated to reflux under a nitrogen atmosphere and maintained at reflux overnight. The mixture was then cooled, diluted with 100 milliliters of water and the pH was adjusted to about 5 with concentrated hydrochloric acid. The mixture was then partitioned between chloroform/water and the organic portion was dried over anhydrous magnesium sulfate and filtered. The filtrate was concentrated in vacuo affording 0.89 grams of white foam confirmed by NMR and MS as the desired product.

EXAMPLE III

Preparation of:
3-Isopropyl-3-Methyl-9-(1-Nitro-1-n-Pentyl-Methyl)-5H-Imidazo-[2,1a]-Isoindoline-2-(3H, 9H)-5-Dione A mixture of 1.48 grams (6.12 mmoles) of 3-isopropyl-3-methyl-5H-imidazo-[2, 1a]-Isoindoline-2-(3H, 9H)-5-dione, 2.00 grams (15.3 mmoles) of nitrohexane, 2.70 grams (19.5 mmoles) of potassium carbonate and 50 milliliters of dimethyl sulfoxide was stirred at room temperature under a nitrogen atmosphere for 24 hours. (After about 2 hours, the originally dark pink mixture turned yellow). The mixture was then diluted with water, the pH was adjusted to about 5 with concentrated hydrochloric acid, and extracted with 2×125 milliliter portions of methylene chloride. The organic extracts were washed with 2×100 milliliter portions of water and 1×100 milliliter portion of aqueous sodium bicarbonate solution. The washed organic extracts were contracted in vacuo giving a pale yellow gum which was crystallized then recrystallized from diethyl ether affording 0.5 gram of fluffy white solid confirmed by NMR and MS as the desired product.

EXAMPLE IV

Preparation of: 3-Isopropyl-3-Methyl-9-(1-Nitro-1-Ethylmethyl)-5H-Imidazo-[2, 1a]-Isoindoline-2-(3H, 9H)-5 -Dione A mixture of 1.00 gram (4.13 mmoles) of 3-isopropyl-3-methyl-5H-imidazo-[2, 1a]-isoindoline-2-(3H, 9H)-5-dione, 0.993 gram (11.16 mmoles) of 1-nitropropane, 1.77 gram (12.80 mmoles) of potassium carbonate and 50 milliliters of dry dimethyl sulfoxide was stirred overnight under a nitrogen atmosphere. The mixture was then diluted with 200 milliliters of water and was acidified to pH 4-5 with concentrated hydrochloric acid. The mixture was then extracted with 3×100 milliliter portions of methylene chloride, the organic extracts were washed with 2×100 milliliter portions of water, dried over anhydrous magnesium sulfate and filtered. The filtrate was concentrated in vacuo giving 1.00 gram of white solid, which upon purification by column chromatography, afforded 0.90 gram of white microcrystalline solid confirmed by NMR and MS as the desired product.

EXAMPLE V

Preparation of: 3-Isopropyl-3-Methyl-9-[(alpha, alpha-Dimethyl)-Nitromethyl]-5-H-Imidazo-[1'2':1,2]-Pyrrolo-[3,4b]-Pyridine-2-[3H, 9H]-5-Dione To a slurry of 0.102 gram (4.25 mmoles) of sodium hydride in 40 milliliters of dry tetrahydrofuran were added 1.72 grams (19.3 mmoles) of 2-nitropropane. 1.00 gram (4.12 mmoles) of 3-isopropyl-3-methyl-5H-imidazo-[1'2':1,2]-pyrrolo-[3,4b]-pyridine-2-(3H, 9H)-5-dione in 20 milliliters of dry tetrahydrofuran was then added over a period of 10 minutes. The stirred mixture was then heated to reflux and maintained at reflux overnight under a nitrogen atmosphere. The mixture was then quenched by the addition of 100 milliliters of water and acidified to pH 5 with concentrated hydrochloric acid. The mixture was then extracted with 2×100 milliliter portions of methylene chloride and the organic extracts were dried over anhydrous magnesium sulfate and filtered. The filtrate was concentrated in vacuo affording 0.27 gram of white foam which, upon purification by column chromatography, was confirmed by NMR and MS as the desired product.

EXAMPLE VI

Preparation of:
3-Isopropyl-3-Methyl-9-Nitromethyl-5H-Imidazo-[2, 1a]-Isoindoline-2-(3H, 9H)-5-Dione A mixture of 1.5 grams (6.20 mmoles) of 3-isopropyl-3-methyl-5H-imidazo-[2, 1a]-isoindoline-2-(3H, 9H)-5-dione, 1.00 gram (16.39 mmoles) of nitromethane, 2.71 grams (19.67 mmoles) of potassium carbonate and 50 milliliters of dry dimethyl sulfoxide was stirred overnight at room temperature under a nitrogen atmosphere. The mixture was then poured into water and the pH was adjusted to 4-5 with hydrochloric acid. The mixture was then extracted with methylene chloride, the organic extract was washed with water, then dried over anhydrous magnesium sulfate and filtered. The filtrate was concentrated in vacuo affording 1.58 grams of pale yellow foam, the NMR of which was consistent with the desired structure. Further purification consisting of dissolution in methylene chloride, washing with aqueous sodium bicarbonate solution, solvent stripping and recrystallization from diethyl ether afforded a solid material (m.p. 154°-155° C.) and confirmed by NMR and MS as the desired material.

EXAMPLE VII

Preparation of:
3-Isopropyl-3-Methyl-9-(1-nitro-1-n-Pentyl-methyl)-55H-Imidazo[1'2':1,2]-Pyrrolo-[3,4b]-Pyridine -2-(3H, 9H)-5-Dione A mixture of 1.50 grams (6.17 mmoles) of 3-isopropyl-3-methyl-5-H-imidazo-[1',2':1,2]-pyrrolo-[3,4b]-pyridine-2-(3H, 9H)-5-dione, 2.00 grams (15.3 mmoles) of nitrohexane, 2.70 grams (19.5 mmoles) of potassium carbonate and 50 milliliters of dry dimethyl sulfoxide was stirred overnight at room temperature under anhydrous conditions, the mixture changing color from pink to yellow. The mixture was quenched in 250 milliliters of water and acidified to pH 6 with concentrated hydrochloric acid. The mixture was then extracted with 2×150 milliliter portions of methylene chloride. The organic extracts were washed with 2×100 milliliter portions of water, dried over anhydrous magnesium sulfate and filtered. The filtrate was concentrated in vacuo affording 2.02 grams of yellow oil to which was added a 1:1 V/V mixture of hexane:diethyl ether and the resulting mixture was allowed to stand quiescent overnight, resulting in formation of 0.130 gram of white solid which was isolated by suction filtration. The filtrate was concentrated in vacuo, triturated with hexane/diethyl ether resulting in formation of 0.47 gram of yellow solid which was combined with the previously isolated solid. The combined solids were purified by column chromatography affording 0.110 gram of white solid confirmed by NMR and MS as the desired product.

The invention compounds prepared as described in the foregoing Examples are of the structural formula depicted in FIG. IV wherein: X, $R^4$ and $R^5$ are as follows:

| Example | X | $R^4$ | $R^5$ |
| --- | --- | --- | --- |
| I | N | H | H |
| II | N | $CH_2CH_3$ | H |
| III | CH | $C_5H_{11}$ | H |
| IV | CH | $CH_2CH_3$ | H |
| V | N | $CH_3$ | $CH_3$ |
| VI | CH | H | H |
| VII | N | $C_5H_{11}$ | H |

Although the invention has been illustrated by the foregoing Examples with regard to the preparation of certain compounds within the scope of Formula I, it is to be understood that other compounds within the scope of Formula I may readily be prepared by those skilled in the art simply by varying the choice of starting materials and using the same or similar techniques.

Weed control in accordance with this invention is effected by applying to the soil prior to emergence of weeds therefrom or to the plant surfaces subsequent to emergence from the soil, a herbicidally effective amount of a compound of this invention. It is, of course, to be understood that the term "a compound of this invention" also includes mixtures of such compounds or a formulation containing a compound or mixture of compounds of this invention.

The term "herbicidally effective amount" is that amount of a compound of this invention required to so injure or damage weeds such that the weeds are incapable of recovering following application while not causing substantial injury to any valuable crop amongst which the weeds might be growing. The quantity of a compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, as little as 1.0 or less pound per acre of a compound of this invention would be expected to provide satisfactory weed control, although in some instances application rates in excess of 1.0 per acre, e.g., up to 2.0 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.1 to 0.5 pound per acre.

Of course, a compound of this invention can be formulated according to routine methods with any of several known and commonly used herbicidal diluents, adjuvants and carriers. The formulations can contain liquid carriers and adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegatative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Science Society of America*, may be used in combination with a compound or compounds of the invention. Typically such formulations will contain from about 5 to about 95 percent by weight of a compound of this invention.

The herbicidal formulations contemplated herein can be applied by any of several method known to the art. Generally, the formulation will be surfaced applied as an aqueous spray. Such application can be carried out by conventional ground equipment, or if desired, the sprays can be aerially applied. Soil incorporation of such surface applied herbicides is accomplished by natural leaching, and is of course facilitate by natural rainfall and melting snow. If desired, however, the herbicides can be incorporated into the soil by conventional tillage means.

Compounds of this invention are believed effective for Preemergence or postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Also controlled by the compounds of this invention are perennials such as quackgrass, Johnsongrass, Canada thistle, curly dock, field chickweed, dandelion, Russian knapweed aster, horsetail, ironweed, sesbania, cattail, wintercress, horsenettle, nutsedge, milkweed, sicklepod, and the like.

The compounds prepared as described in the Examples were individually screened for herbicidal efficacy, against a variety of weed species, under controlled laboratory conditions of light, humidity and temperature. Solvent solutions of said compounds were applied, both preemergence and postemergence, to test flats containing the various weed species, and herbicidal efficacy was determined by periodic visual inspection, after application of the compounds. Herbicidal efficacy was determined on a Numerical Injury Rating (NIR) scale of from 0 (no injury) to 10 (all plants dead). A NIR rating of 7–9 indicates severe injury; a NIR rating of 4–6 indicates moderate injury, i.e., plant growth is reduced to the extent that normal growth would be expected only under ideal conditions; and a NIR rating of 1–3 indicates slight injury.

For example, the following table gives the preemergence and postemergence NIR determined for the compounds prepared as described in Examples I and II on the weed species to which the compounds were applied. Each compound was applied at a rate of 0.5 pound per acre and the NIR was determined two weeks subsequent to application.

|  | Preemergence | | Postemergence | |
| --- | --- | --- | --- | --- |
|  | I | II | I | II |
| Teaweed | 9 | 9 | 8 | 8 |
| Jimsonweed | 2 | 9 | 10 | 10 |
| Sicklepod | 9 | 9 | 7 | 9 |
| Lambsquarter | 8 | 9 | 9 | 9 |
| Yellow Foxtail | 8 | 8 | 7 | 8 |
| Yellow Nutsedge | 10 | 10 | — | — |
| Johnsongrass | 8 | 8 | 9 | 9 |
| Coffeeweed | 8 | 8 | 8 | 9 |
| Velvet Leaf | 9 | 9 | 9 | 9 |
| Tall Morningglory | 9 | 9 | 8 | 9 |
| Wild Oats | 8 | 8 | 8 | 9 |
| Barnyardgrass | 8 | 9 | 8 | 9 |

Although the invention has been described in considerable detail by the foregoing, it is to be understood that many variations may be made therein by those skilled in the art without departing from the spirit and scope thereof as defined by the appended claims.

I claim:

1. A compound of the formula:

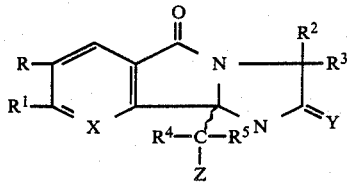

wherein:
R and $R^1$ are the same or different and represent hydrogen, halogen, $C_1$ to $C_4$ alkyl, alkoxy, alkylthio or haloalkyl; up to $C_6$ alkenyl or alkynyl; phenyl or phenyl alkyl;

$R^2$ and $R^3$ are the same or different and represent $C_1$ to $C_4$ alkyl, haloalkyl or alkoxy;

X is CH or nitrogen;

Y is oxygen or sulfur;

Z is nitro, amino, cyano or —$COOR^6$ wherein $R^6$ is hydrogen, alkali metal or $C_1$ to $C_4$ alkyl;

$R^4$ is hydrogen, $C_1$ to $C_4$ alkyl, haloalkyl, alkoxy or alkylthio, or up to $C_6$ alkenyl or alkynyl; and $R^5$ is Z or $R^4$.

2. A compound as defined in claim 1 wherein R and $R^1$ are hydrogen; $R^2$ and $R^3$ are alkyl, Y is oxygen; Z is nitro; and $R^4$ and $R^5$ are independently hydrogen or alkyl.

3. A herbicidal composition containing an inert carrier and a herbically effective amount of a compound or mixture of compounds defined by claim 1.

4. In a method of controlling vegetative growth by applying to the locus of the vegetative growth a growth controlling amount of a growth controlling chemical wherein the improvement resides in using as the growth controlling chemical a compound or mixture of compounds defined by claim 1.

* * * * *